United States Patent
Kamikubo et al.

[11] Patent Number: 6,123,763
[45] Date of Patent: Sep. 26, 2000

[54] PIGMENT DISPERSING AGENT AND PIGMENT COMPOSITION CONTAINING THE SAME

[75] Inventors: Takashi Kamikubo; Yuuji Hirasawa; Toru Omura, all of Tokyo, Japan

[73] Assignee: Toyo Ink Mfg. Co., Ltd., Tokyo, Japan

[21] Appl. No.: 09/233,045

[22] Filed: Jan. 20, 1999

[51] Int. Cl.[7] .......................... C09B 67/00; C09D 17/00; C09D 7/02

[52] U.S. Cl. .......................... 106/506; 106/413; 106/414; 106/429; 106/448; 106/452; 106/453; 106/460; 106/476; 106/493; 106/494; 106/495; 106/496; 106/497; 106/498; 106/499

[58] Field of Search ................... 106/493, 494, 106/495, 496, 497, 498, 499, 506, 413, 414, 429, 448, 452, 453, 460, 476

[56] References Cited

U.S. PATENT DOCUMENTS

| | | | |
|---|---|---|---|
| 4,517,357 | 5/1985 | Kunde et al. | 534/605 |
| 5,112,404 | 5/1992 | Sommer et al. | 106/506 |
| 5,786,459 | 7/1998 | Stöhr et al. | 534/797 |

FOREIGN PATENT DOCUMENTS

| | | |
|---|---|---|
| 0 062 824 | 10/1982 | European Pat. Off. . |
| 0 074 589 | 3/1983 | European Pat. Off. . |
| 0 308 800 | 3/1989 | European Pat. Off. . |
| 0 710 706 | 5/1996 | European Pat. Off. . |
| 0 753 542 | 1/1997 | European Pat. Off. . |
| 32 22 965 | 12/1983 | Germany . |
| 2149808 | 6/1985 | United Kingdom . |
| 2158837 | 11/1985 | United Kingdom . |
| 2191210 | 12/1987 | United Kingdom . |
| 2266893 | 11/1993 | United Kingdom . |

OTHER PUBLICATIONS

*Chemical Abstracts*, 111(4), abstract No. 25008g (abstract of JP 63–305173) (Dec. 1988).
*Chemical Abstracts*, 109(26), abstract No. 232743s (abstract of JP 63–099383) (Apr. 1988).
*Chemical Abstracts*, 106(22), abstract No. 178189p (abstract of JP 61–246261) (Nov. 1986).

*Primary Examiner*—Anthony Green
*Attorney, Agent, or Firm*—Wenderoth, Lind & Ponack, L.L.P.

[57] ABSTRACT

A colorless or only slightly colored pigment dispersing agent which is feasible as a pigment dispersing agent for pigments having various hues and has the general formula (1),

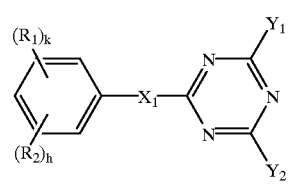

(1)

wherein $R_1, R_2, X_1, Y_1, Y_2$, k and h are as defined in claim 1.

4 Claims, No Drawings

PIGMENT DISPERSING AGENT AND PIGMENT COMPOSITION CONTAINING THE SAME

FIELD OF THE INVENTION

The present invention relates to a pigment dispersing agent excellent in suitability in use, particularly excellent in freedom of aggregation, non-crystallizability and fluidity, and more specifically, it relates to a pigment dispersing agent effective for an ink and a coating composition and a pigment composition containing the same.

PRIOR ART OF THE INVENTION

In a coating composition or an ink composition, generally, a pigment which exhibits a clear color tone and a high tinting strength is formed of fine particles. When fine particles of a pigment are dispersed in a non-aqueous vehicle for an offset ink, a gravure ink or a coating composition, it is difficult to obtain a stable dispersion, and it is known that the dispersion is therefore stabilized by improving the affinity between the pigment and the vehicle with a pigment dispersing agent.

Many proposals of pigment dispersing agents of the above type have been so far published with regard to pigments among which copper phthalocyanine and quinacridone pigments are mainly there.

As is typically disclosed in Japanese Patent Publication No. 41-2466 and U.S. Pat. No. 2,855,403, there are known methods of incorporating compounds obtained by introducing a side-chain substituent selected from sulfonic acid, a sulfoneamide group, an aminomethyl group or a phthalimidemethyl group into an organic pigment as a matrix structure. These compounds have a high effect on the freedom of aggregation and the stability against crystallization. Since, however, the compound which is to be incorporated is derived from a compound having the same chemical structure as the structure of a pigment, it has inherent intense coloring properties and is therefore extremely limited when applied to a pigment having a different hue. It is therefore required to provide compounds corresponding to individual pigments, which requirement is appreciably disadvantageous for producing pigment compositions. Further, when a substituent is introduced as a side chain to a pigment for the preparation of the above compounds, it is required to dissolve the pigment in concentrated sulfuric acid or fuming sulfuric acid or react chlorosulfonic acid with the pigment, in order to introduce a reactive group. Since concentrated sulfuric acid or fuming sulfuric acid is dangerous and difficult to handle, and limitations are imposed on production facilities and an output of production, which limitations are disadvantageous for the production.

SUMMARY OF THE INVENTION

It is an object of the present invention to provide a colorless or only slightly colored pigment dispersing agent feasible as a pigment dispersing agent for pigments having various hues.

It is another object of the present invention to provide a pigment dispersing agent having a matrix structure other than an organic pigment.

It is further another object of the present invention to provide a pigment composition capable of providing an ink or a coating composition excellent in the freedom of aggregation, non-crystallizability and fluidity, and a pigment composition containing a pigment dispersing agent capable of providing the above pigment composition.

According to the present invention, there is provided a pigment dispersing agent of the general formula (1),

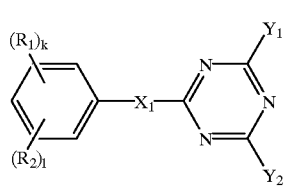

(1)

wherein $X_1$ is —$NR_3$ or —O—, $R_1$ is an amino group, $R_2$ is a halogen atom, an amino group, a nitro group, a hydroxyl group, an alkoxy group, a carboxyl group, a sulfonic acid group, a substituted or non-substituted alkyl group or a substituted or non-substituted alkenyl group, $R_3$ is a hydrogen atom, a substituted or non-substituted alkyl group or a substituted or non-substituted alkenyl group, $Y_1$ is any one of groups of the general formulae (2) to (5), $Y_2$ is a hydroxyl group, an alkoxy group, $Y_1$ or a group of the general formula (6), k is an integer of 1 to 3, and l is an integer of 0 to 2, General formula (2):

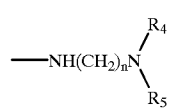

(2)

wherein each of $R_4$ and $R_5$ is independently substituted or non-substituted alkyl group or a substituted or non-substituted alkenyl group or they form a five- or six-membered ring which may contain a nitrogen atom, an oxygen atom or a sulfur atom, and n is an integer of 1 to 6, General formula (3):

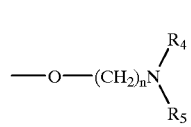

(3)

wherein $R_4$ and $R_5$ are as defined in the general formula (2),
General formula (4):

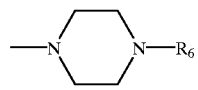

(4)

wherein $R_6$ is a substituted or non-substituted alkyl group or a substituted or non-substituted alkenyl group,
General formula (5):

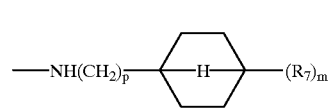

(5)

wherein $R_7$ represents a group of the general formula (4) or a group of the general formula (7), p is an integer of 0 to 6 and m is an integer of 1 or 2, General formula (6):

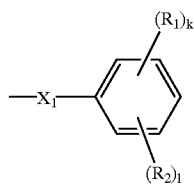

(6)

wherein $X_1$, $R_1$, $R_2$, k and l are as defined in the general formula (1),

General formula (7):

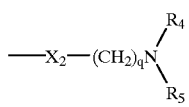

(7)

wherein $X_2$ is a direct bond, —NH— or —O—, q is an integer of 0 to 6 and $R_4$ and $R_5$ are as defined in the general formula (2).

According to the present invention, there is also provided a pigment composition containing a pigment and the above pigment dispersing agent.

DETAILED DESCRIPTION OF THE INVENTION

The present invention will be explained in detail hereinafter.

The pigment dispersing agent of the present invention has a triazine ring, an aromatic amino group and an amino group represented by $Y_1$ in the general formula (1), i.e., a substituent represented by one of the general formulae (2) to (5).

The alkoxy group included in each of $R_2$ and $Y_2$ in the general formula (1) is preferably an alkoxy group having 1 to 20 carbon atoms, and examples thereof include methoxy, ethoxy, n-propoxy, isopropoxy, n-butoxy, isobutoxy, pentoxy, hexoxy, etc.

The substituted or non-substituted alkyl or the substituted or non-substituted alkenyl group included in each of $R_2$, $X_1$ and $Y_1$ in the general formula (1) is preferably a substituted or non-substituted alkyl or alkenyl group having 1 to 20 carbon atoms. Examples of the non-substituted alkyl group include methyl, ethyl, n-propyl, isopropyl, n-butyl, isobutyl, pentyl, hexyl, etc. Examples of the non-substituted alkenyl group include vinyl, 1-propenyl, 2-propenyl, isopropenyl, 1-butenyl, 2-butenyl, 2-pentenyl, 2-methylallyl, etc. The substituted alkyl or alkenyl group refers to an alkyl or alkenyl group of which the hydrogen atom is replaced with a halogen such as a chlorine atom or a bromine atom, a hydroxyl group or a mercapto group. Further, a combination of $R_4$ and $R_5$ may be a five- or six-membered ring which alkyl groups together form and which may further contain a nitrogen atom, an oxygen atom or a sulfur atom. Examples of the above five- or six-membered ring include the following substituents.

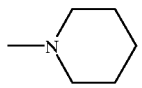

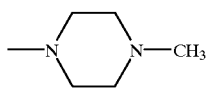

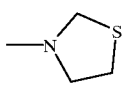

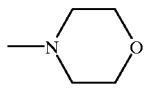

Of these, $Y_1$ is preferably a group of the general formula (2), and further, each of $R_4$ and $R_5$ is preferably an alkyl group having 1 to 6 carbon atoms.

The benzene ring of the pigment dispersing agent of the present invention may have a substituent represented by R2 in a position where it can be substituted, in addition to the amino group represented by $R_1$ in the general formula (1). That is, the benzene ring may contain any substituent selected from a halogen atom, an amino group, a nitro group, a hydroxyl group, an alkoxy group, a carboxyl group, a sulfonic acid group, a substituted or non-substituted alkyl group or a substituted or non-substituted alkenyl group, and the above substituent is not specially limited in kind. Further, the benzene ring may have a plurality of the above substituents, and in this case, one substituent may be the same as, or different from, the other or others.

The pigment dispersing agent of the present invention has been explained with regard to its structure hereinabove, and examples of the pigment dispersing agent of the present invention include the following compounds.

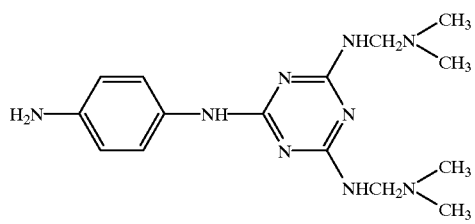

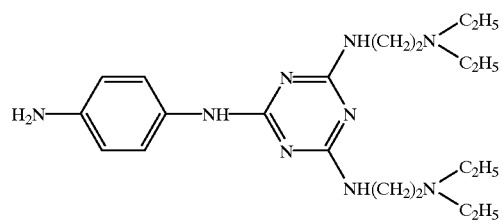

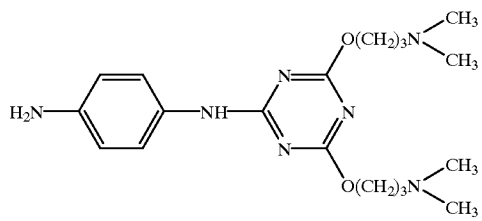
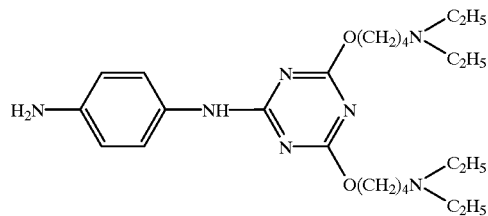
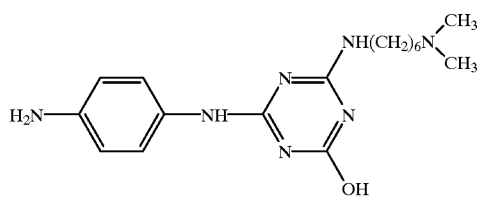
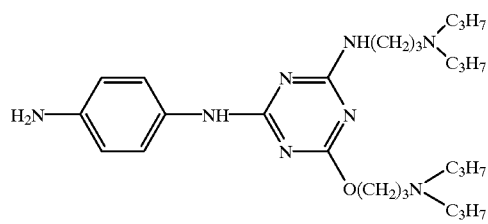
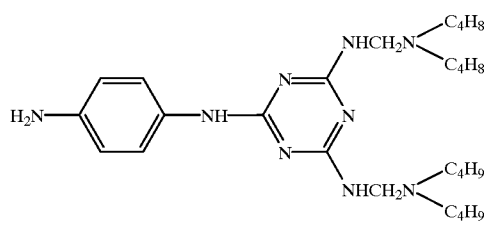
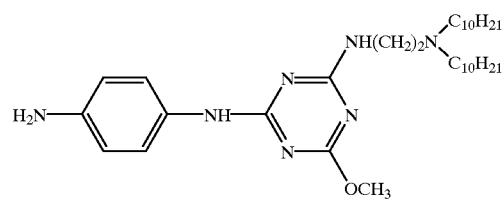
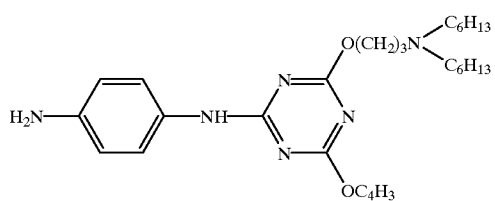
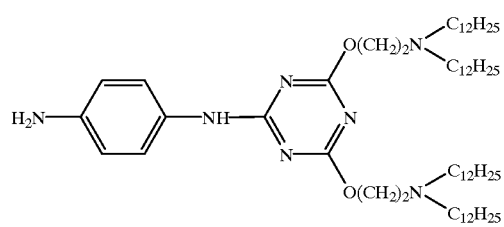
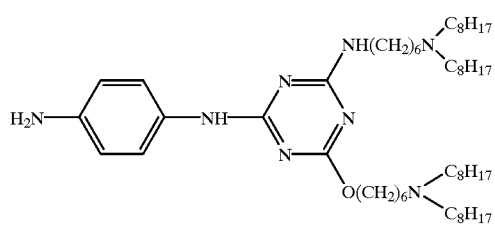
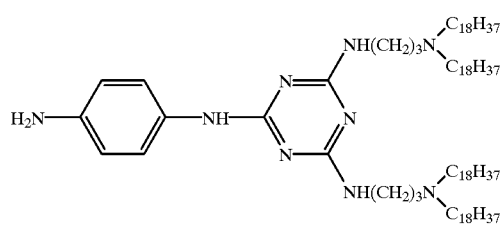
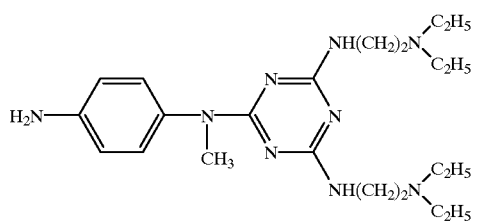
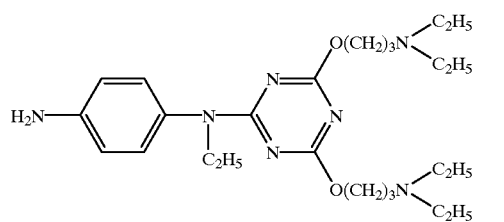

-continued
7
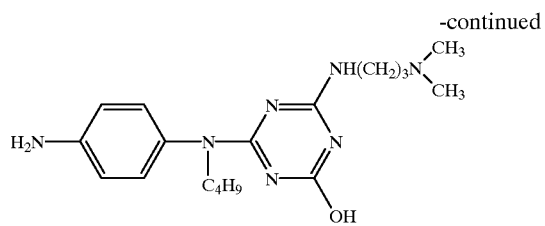
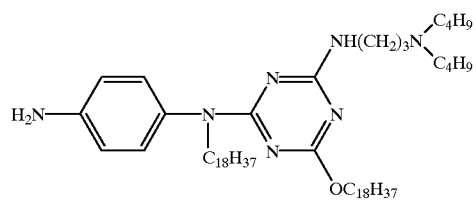
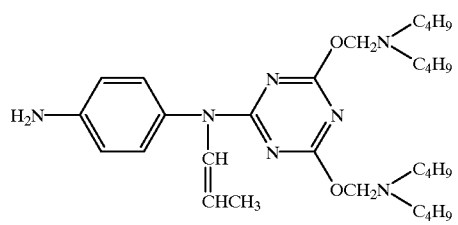
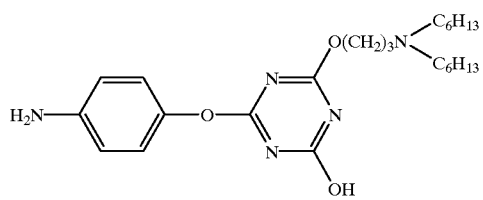
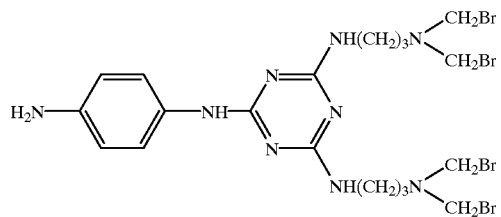
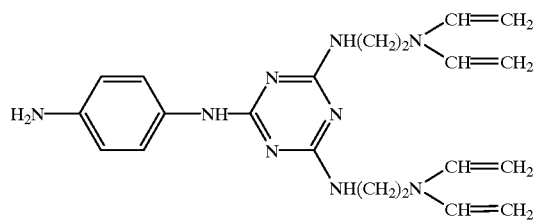
8
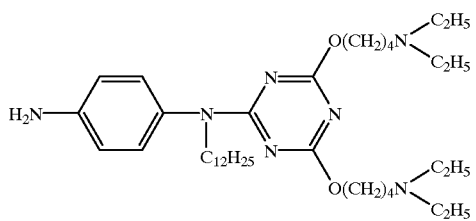
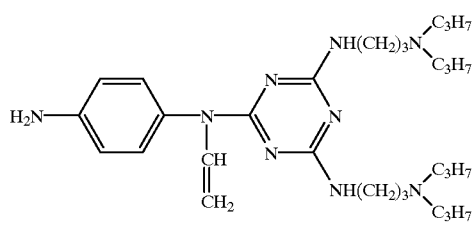
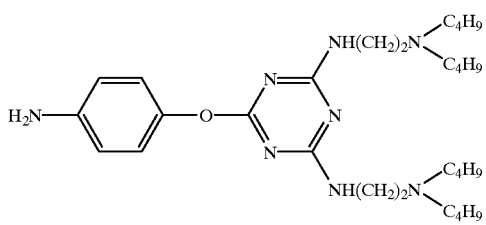
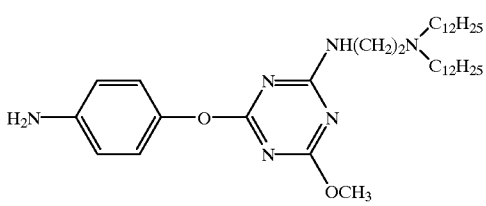
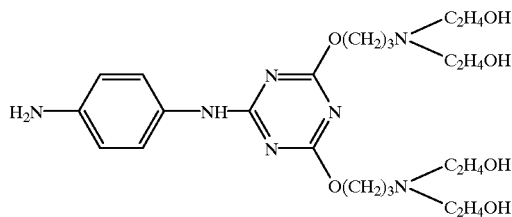
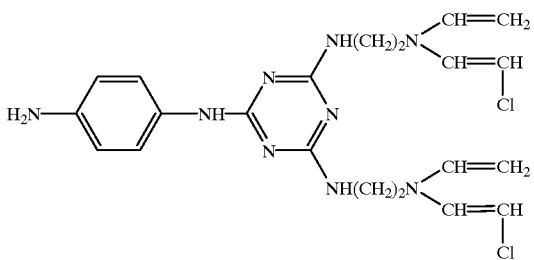

-continued
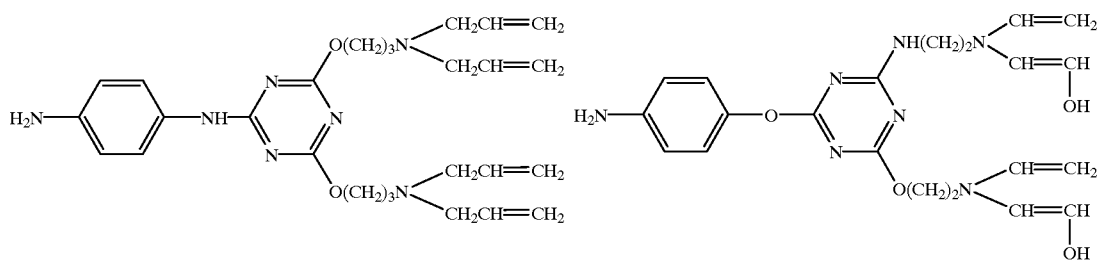
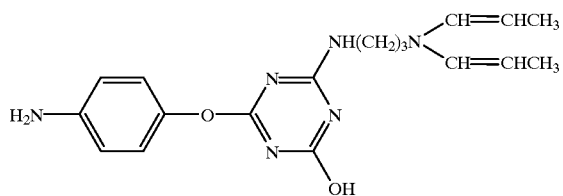
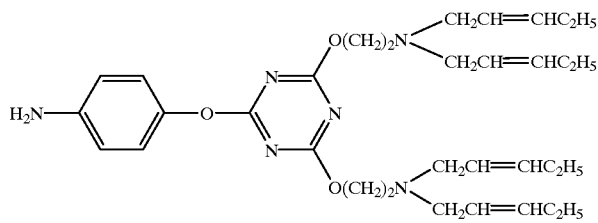
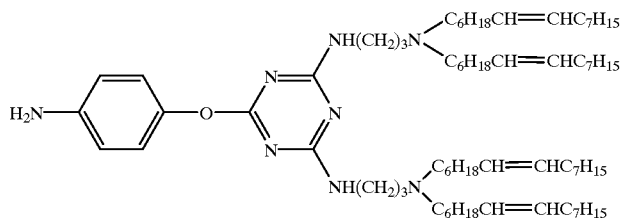
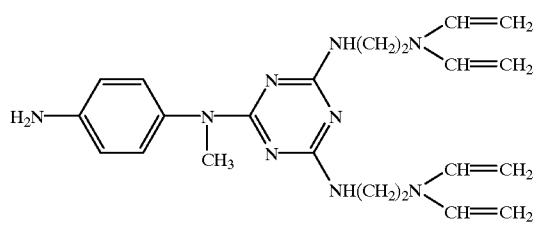
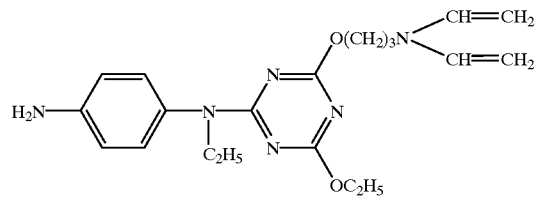
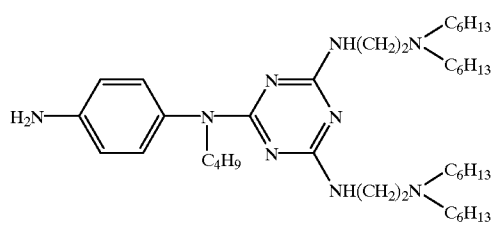
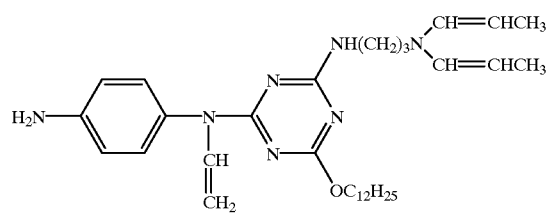

| 11 | 12 |
|---|---|
| 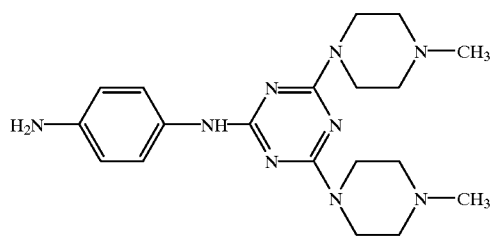 | 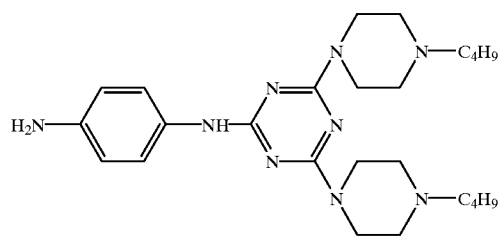 |
| 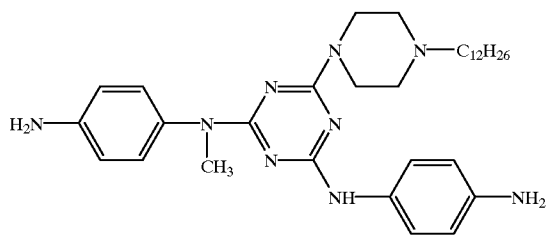 | 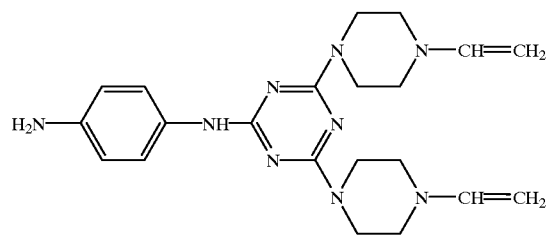 |
| 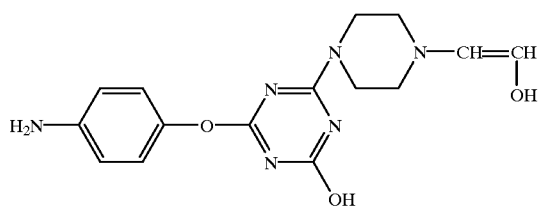 | 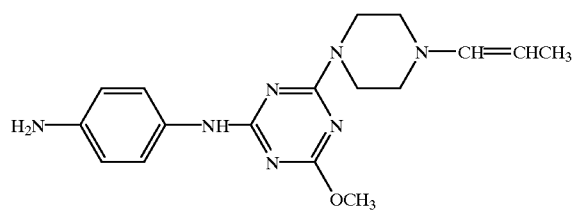 |
| 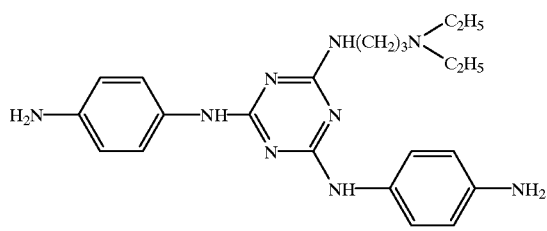 | 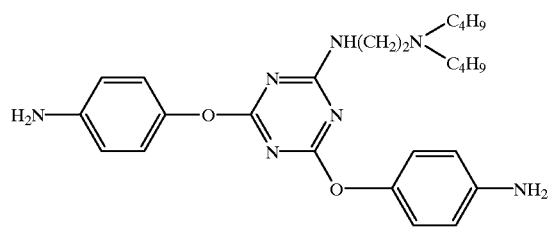 |
| 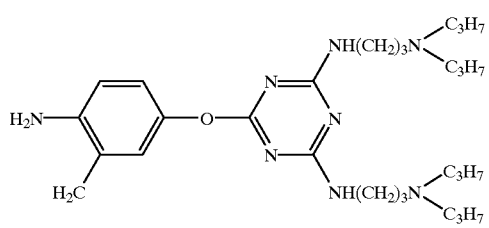 | 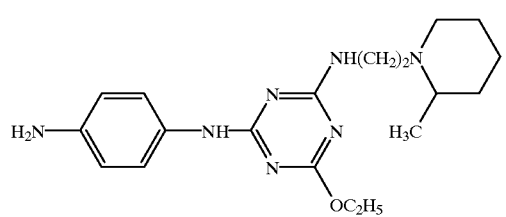 |
| 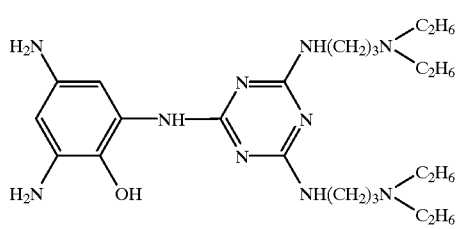 | 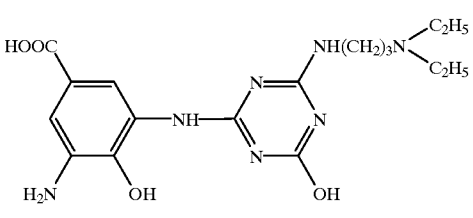 |

-continued
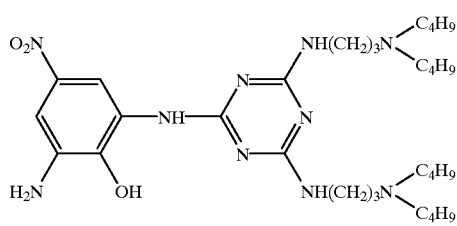
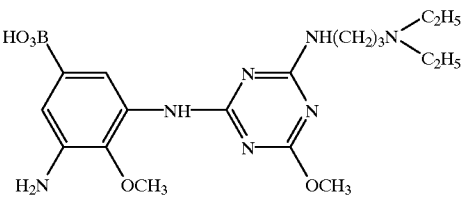
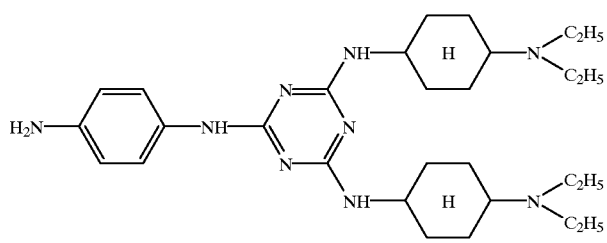
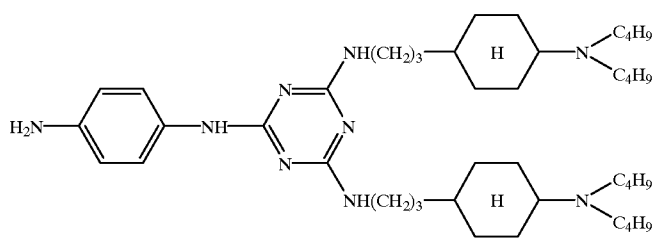
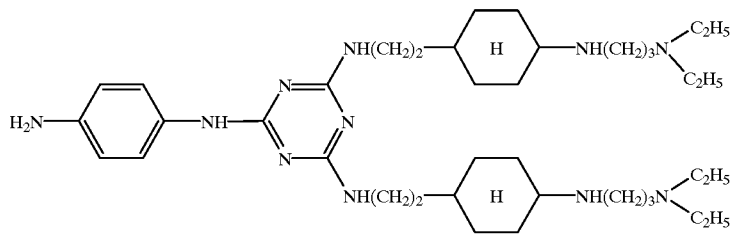
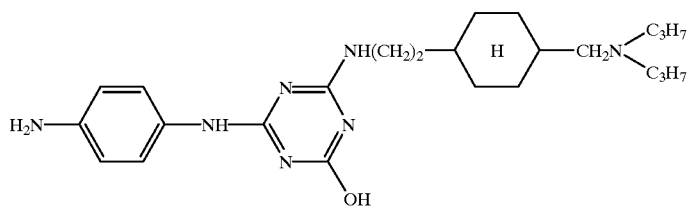

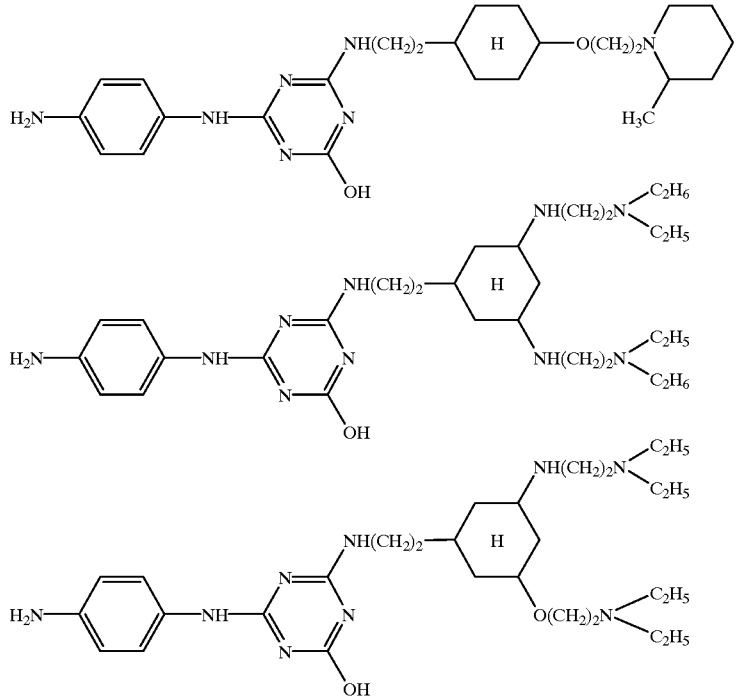

The pigment dispersing agent of the present invention can be produced, for example, by the following method. First, equimolar amounts of p-aminoacetoanilide and cyanuric chloride are allowed to react in water, an acetic acid aqueous solution, an alcohol, a mixture of water with an alcohol or a general organic solvent such as xylol, to obtain a compound (8) of the following formula.

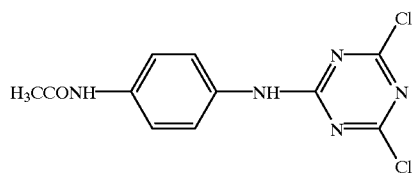
(8)

Then, for introducing $Y_1$ and $Y_2$, a compound of any one of the general formulae (9) to (12) is reacted with the compound (8) in water or a general organic solvent, to prepare a compound of one of the general formulae (13) to (16).

General formula (9)

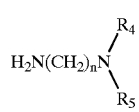
(9)

General formula (10)

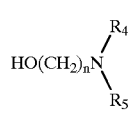
(10)

General formula (11)

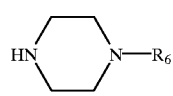
(11)

General formula (12)

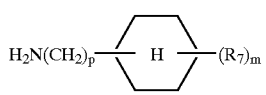
(12)

General formula (13)

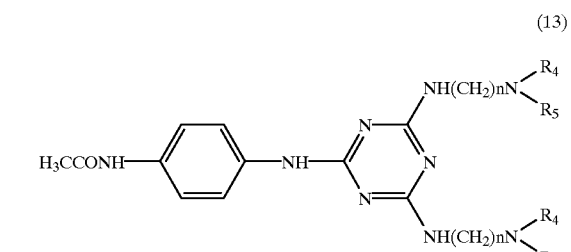
(13)

General formula (14)

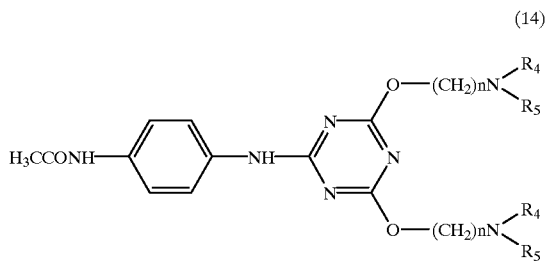

General formula (15)

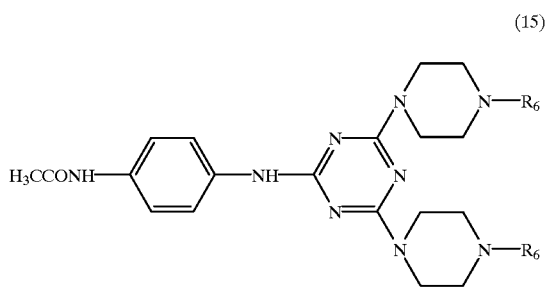

General formula (16)

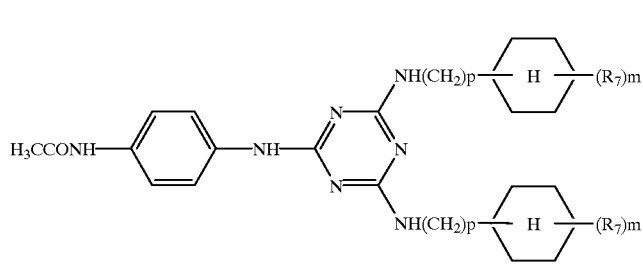

In the above formulae, $R_4$, $R_5$, $R_6$, $R_7$, m, n and p are as defined in the general formula (1).

Then, the compound of the general formula (13), (14), (15) or (16) is hydrolyzed in the presence of a hydrochloric acid aqueous solution or the like, whereby the pigment dispersing agent of the general formula (1), provided by the present invention, can be obtained.

In another method, p-nitro-aniline is used in place of p-amino-acetonitrile, to obtain a compound (17) of the following formula, the compound (17) is reacted with a compound of any one of the general formulae (9) to (12), and then a nitro group is reduced, whereby the pigment dispersing agent of the general formula (1), provided by the present invention, can be also obtained.

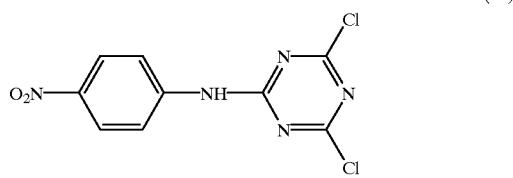

The compound (8) or the compound (17) may be hydrolyzed in the position of one chlorine atom during the reaction to have a hyroxyl group or an alkoxy group, while a pigment dispersing agent obtained as an end product can be used as a pigment dispersing agent of the present invention.

Example of the general formula (9) used in the present invention include N,N-dimethylaminoethylamine, N,N-diethylaminoethylamine, N,N-dibutylaminoethylamine, N,N-dimethylaminopropylamine, N,N-diethylaminopropylamine, N,N-dibutylaminopropylamine, N,N-dimethylaminobutylamine, N,N-diethylaminobutylamine, N,N-dipropylaminobutylamine, N,N-dibutylaminobutylamine, N,N-diethylaminohexylamine, N-aminomethylpiperidine, N,N-aminoethylpiperidine, N-aminopropylpiperidine, N-aminoethylpyrrolidine, N-aminopropylpyrrolidone, N-aminomethyl-2-pipecoline, N-aminoethyl-4-pipecoline, N-aminopropyl-2-pipecoline, N-aminoethylmorpholine, N-aminopropylmorpholine, N,N-methyllaurylaminopropylamine, N,N-dioleylaminoethylamine and N,N-distearylaminobutylamine.

Examples of the compound of the general formula (10) used in the present invention include N,N-dimethylaminomethanol, N,N-dimethylaminoethanol, N,N-diethylaminoethanol, N,N-dibutylaminomethanol, N,N-dibutylaminoethanol, N,N-dibutylaminopropanol, N,N-diethylaminobutanol, N,N-dioleylbutanol, N-hydroxyethylpiperidine, N-hydroxypropylpiperidine, N-hydroxyethylpipecoline, N-hydroxypropylpipecoline, N-hydroxymethylpyrrolidine, N-hydroxybutylpyrrolidine, N-hydroxyethylmorpholine and N-hydroxybutylmorpholine.

Examples of the compound of the general formula (11) used in the present invention include N-methylpiperazine, N-ethylpiperazine, N-butylpiperazine and 1-cyclopentylpiperazine.

Examples of the compound of the general formula (12) used in the present invention include 1-amino-4-N,N-dimethylaminocyclohexane, 1-amino-4-N,N-diethylaminocyclohexane, 1-amino-4-N,N-dibutyaminocyclohexane, 1-aminomethyl-4-N,N-dimethylaminocyclohexane, 1-aminomethyl-4-N,N-diethylaminocyclohexane, 1-aminomethyl-4-N,N-dibutylaminocyclohexane, 1-aminoethyl-4-N,N-dimethylaminocyclohexane, 1-aminoethyl-4-N,N-diethylaminocyclohexane, 1-aminoethyl-4-N,N-dibutylaminocyclohexane, 1-amino-4-N,N-dimethylaminomethylcyclohexane, 1-amino-4-N,N-dibutylaminomethylcyclohexane, 1-amino-4-N,N-dimethylaminoethylaminocyclohexane, 1-amino-4-N,N-dimethylaminopropylaminocyclohexane, 1-amino-4-N,N-diethylaminoethylaminocyclohexane, 1-amino-3,5-N,N-dimethylaminocyclohexane, 1-amino-3,5-N,N-diethylaminocyclohexane, 1-amino-3,5-N,N-dibutylaminocyclohexane, 1-amino-3,5-N,N-dimethylaminomethylcyclohexane, 1-amino-3,5-N,N-diethylaminomethylcyclohexane, 1-amino-3,5-N,N-dibutylaminomethylcyclohexane, 1-amino-4-N,N- methylpiperazinecyclohexane, 1-amino-4-N-ethylpiperazinecyclohecane and 1-amino-4-N-butylpiperazinecyclochexane.

The pigment dispersing agent obtained in the present invention exhibits excellent effects on all of generally commercially available pigments. For example, it can be applied, for example, to organic pigments such as a phthalocyanine pigment, a quinacridone pigment, an isoindolinone pigment, a perylene-perinone pigment, a dioxadine pigment, a diketopyrrolopyrrole pigment, an anthraquinone pigment, a benzoimidazolone pigment and an azo pigment, and inorganic pigments such as carbon black, titanium oxide, chrome yellow, cadmium yellow, cadmium red, red iron oxide, iron black, flowers of zinc, Prussian blue and ultramarine.

The pigment dispersing agent of the present invention has a colorless or a slightly colored hue, so that it is advantageous in that it causes no or almost no change in hue when added to a variety of pigments and is excellent in use together with almost all pigments.

The pigment composition of the present invention is a composition containing a pigment and the pigment dispersing agent of the general formula (1).

The amount of the pigment dispersing agent of the general formula (1) per 100 parts by weight of the pigment is preferably 0.1 to 30 parts by weight.

When the amount of the pigment dispersing agent of the general formula (1) is less than 0.1 part by weight, undesirably, the effect on dispersing a pigment is low. When it exceeds 30 parts by weight, no further effect can be obtained.

The pigment dispersing agent of the present invention is used, for example, by the following methods.

1. A pigment and the pigment dispersing agent are mixed to obtain a pigment composition in advance, and the pigment composition is dispersed in a non-aqueous vehicle.

2. A pigment and the pigment dispersing agent are separately added to a non-aqueous vehicle, and then dispersed.

3. A pigment is dispersed in a non-aqueous vehicle, the pigment dispersing agent is dispersed in a separate non-aqueous vehicle, and the resultant dispersions are mixed. In this case, the pigment dispersing agent may be dispersed in a solvent alone.

4. A pigment is dispersed in a non-aqueous vehicle to prepare a pigment dispersion, and the pigment dispersing agent is added to the pigment dispersion.

The intended effect can be obtained by any one of the above methods.

In the preparation of the pigment composition, the dispersing effect can be fully obtained by simply mixing a pigment powder and the pigment dispersing agent of the present invention, while superior results can be obtained by mechanically mixing a pigment and the pigment dispersing agent with a kneader, a roll, an attritor, a super mill or other pulverizer, by adding a solution containing the pigment dispersing agent of the present invention to a suspension of a pigment in water or an organic solvent to deposit pigment dispersing agent on the surface of each pigment particle, or by co-dissolving an organic pigment and the pigment dispersing agent in a solvent having high dissolving power such as sulfuric acid and co-precipitating them in a bad solvent such as water.

Further, when a pigment or the pigment dispersing agent is dispersed in, or mixed with, a non-aqueous vehicle or a solvent, a dispersing machine such as a dissolver, a high-speed mixer, a homo-mixer, a kneader, a roll mill, a sand mill or an attritor may be used, and in this case, the pigment can be well dispersed.

According to the present invention, therefore, an excellent fluidity such as a decrease in the viscosity of a dispersion and a decrease in structural viscosity is exhibited as compared with a case using a pigment alone in a non-aqueous vehicle for a gravure ink such as a lime rosin varnish, a polyamide resin varnish or a vinyl chloride resin varnish, an ordinary-drying or baking coating composition such as a nitrocellulose lacquer or an aminoalkyd resin, an acryl lacquer, an aminoacrylic resin baking coating composition or a urethane resin coating composition. At the same time, there is no problems such as color separation or a change in crystal, and a printed product and a coating have excellent gloss so that aesthetically fine products can be obtained.

The pigment dispersing agent and the pigment composition of the present invention are not limited to a mixture with a non-aqueous vehicle, and have an excellent dispersing effect when mixed with other printing ink or coating composition or when used to color plastics.

EXAMPLES

The present invention will be more specifically explained with reference to Examples hereinafter. In Examples, "part" stands for "part by weight", and "%" stands for "% by weight".

Preparation Example 1

20 Parts of p-aminoacetoanilide and 25 parts of cyanuric chloride were added to 300 parts of methanol, and the mixture was allowed to react at 20° C. or lower for 2 hours. Then, 46 parts of N,N-dibutylaminoethylamine was added, and the mixture was refluxed under heat for 2 hours. Then, 100 parts of hydrochloric acid was added for hydrolysis, methanol was then removed, and 40 parts of sodium hydroxide and 1,000 parts of water were added, followed by filtration, washing with water and drying, to give 64 parts of a pigment dispersing agent (a) having the following structure.

Pigment dispersing agent (a)

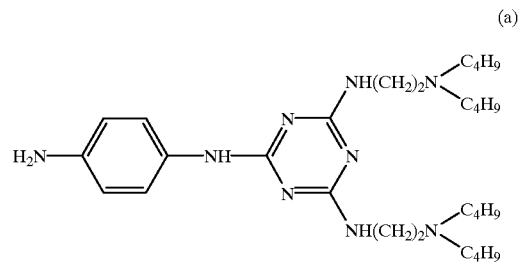

Preparation Example 2

76 Parts of a pigment dispersing agent (b) having the following structure was obtained in the same manner as in Example 1 except that 46 parts of N,N- dibutylaminoethylamine was replaced with 50 parts of N,N-dibutylaminopropanol.

Pigment dispersing agent (b)

(b)

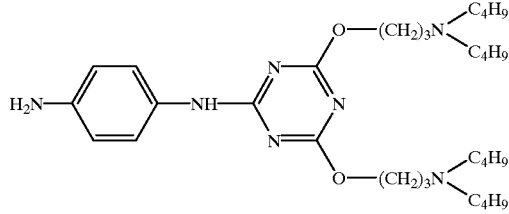

Preparation Example 3

22 Parts of 3-methyl-4-aminoacetoanilide and 25 parts of cyanuric chloride were added to 300 parts of methanol, and the mixture was allowed to react at 20° C. or lower for 2 hours. Then, 12 parts of N,N-dimethylaminoethylamine was added, and the mixture was refluxed under heat for 2 hours. Then, 100 parts of hydrochloric acid was added for hydrolysis, methanol was then removed, and 40 parts of sodium hydroxide and 1,000 parts of water were added, followed by filtration, washing with water and drying, to give 47 parts of a pigment dispersing agent (c) having the following structure.

Pigment dispersing agent (c)

(c)

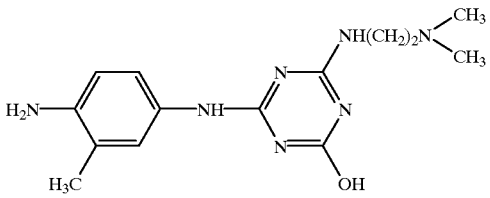

Preparation Example 4

40 Parts of p-aminoacetoanilide and 25 parts of cyanuric chloride were added to 300 parts of methanol, and the mixture was allowed to react at 30° C. for 2 hours. Then, 14 parts of N,N-diethylaminoethylamine was added, and the mixture was refluxed under heat for 2 hours. Then, 100 parts of hydrochloric acid was added for hydrolysis, methanol was then removed, and 40 parts of sodium hydroxide and 1,000 parts of water were added, followed by filtration, washing with water and drying, to give 62 parts of a pigment dispersing agent (d) having the following structure.

Pigment dispersing agent (d)

(d)

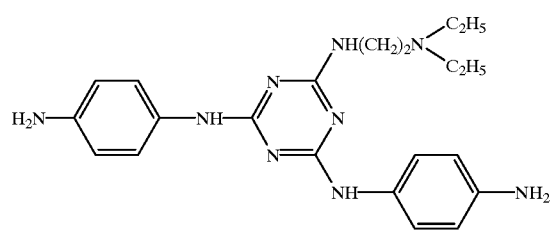

Pigment dispersing agents (e) to (l) having structures shown in Table 1 were synthesized in similar manners.

TABLE 1

| Pigment dispersing agent | Structure of pigment dispersing agent |
|---|---|
| (e) | 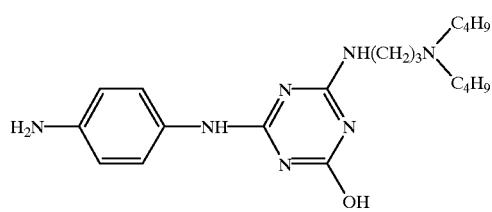 |
| (f) | 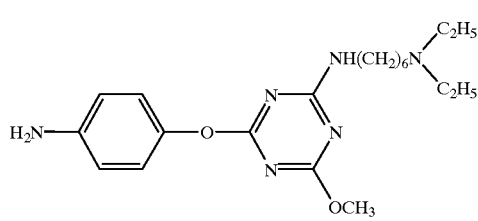 |

TABLE 1-continued
| Pigment dispersing agent | Structure of pigment dispersing agent |
|---|---|
| (g) | 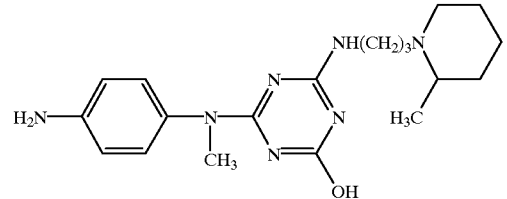 |
| (h) | 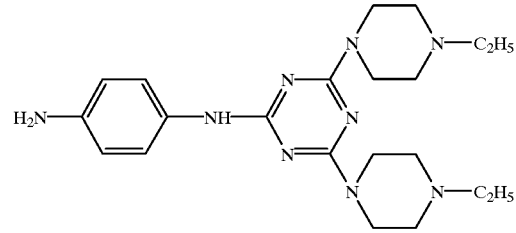 |
| (i) | 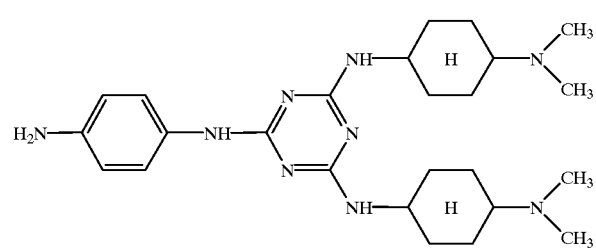 |
| (j) | 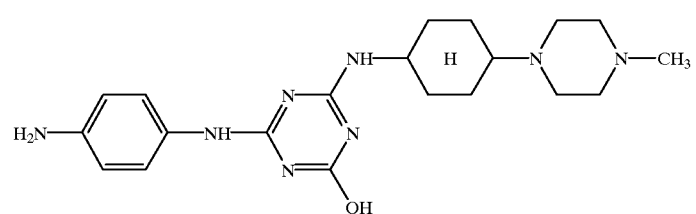 |
| (k) | 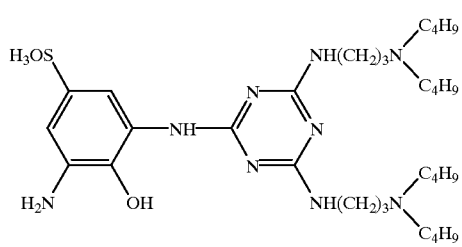 |
| (l) | 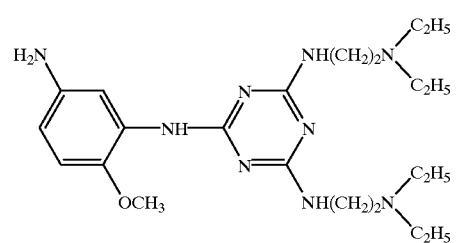 |

Examples 1–21 and Comparative Examples 1–15

Coating compositions were prepared as follows. A pigment alone or a pigment composition containing a pigment, a pigment dispersing agent having a pigment structure and one of the pigment dispersing agents (a) to (l) was dispersed in an aminoalkyd resin varnish for a baking coating composition such that the resultant coating composition had a pigment content of 6%. As a pigment dispersing agent having a pigment structure, the following compound having a copper phthalocyanine structure or a quinacridone structure was used.

Pigment dispersing agent having a copper phthalocyanine structure (m)

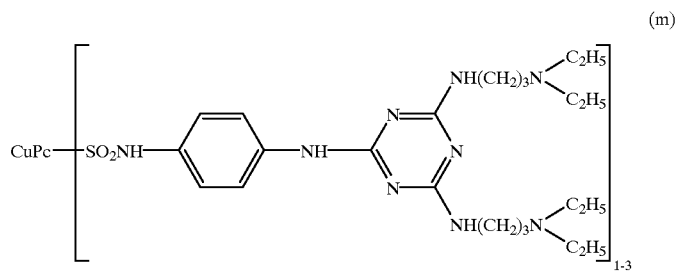

Pigment dispersing agent having a quinacridone structure (n)

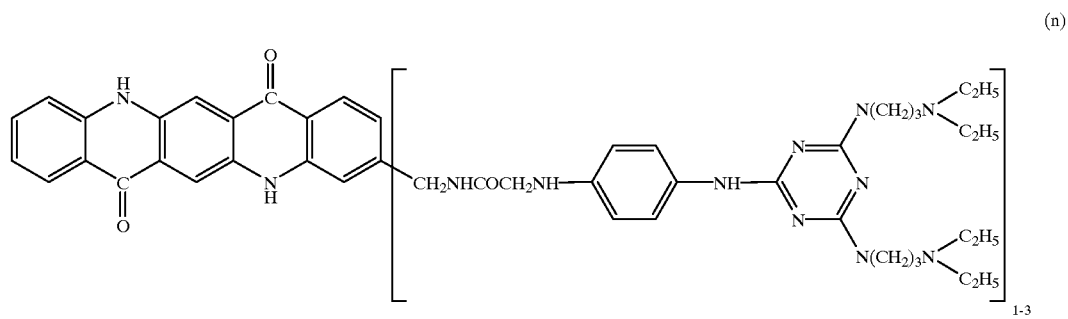

When each of the coating compositions obtained in the above manner was measured for a viscosity, the coating compositions containing the pigment dispersing agents of the present invention had a low viscosity and showed small thixotropic properties (TI values), and they showed excellent fluidity, as shown in Table 2.

Further, the above coating compositions were viscosity-adjusted to show 20 seconds (25° C.) with a ford cup #4, and each of the adjusted coating compositions was air-sprayed to an intermediate-coated plate (steel plate coated with a primer coating composition) so as to form a dry coating having a thickness of about 30 $\mu$m. Each plate was allowed to stand for 10 minutes, and then the coatings were baked at 140° C. for 30 minutes.

As shown in Table 2, the coating compositions containing the pigment dispersing agents of the present invention showed excellent gloss over compositions in Comparative Examples. Further, the coating compositions containing the pigment dispersing agents of the present invention did not foul the hues of matrix pigments and showed hues equivalent to the hues of the pigments alone.

With regard to freedom of aggregation and non-crystallizability, the coating compositions were evaluated for stability against color separation as follows, which is a problem in practical use.

A coating composition was diluted with a base coating composition (prepared by dispersing titanium oxide in an aminoalkyd resin varnish) so as to have a pigment/titanium oxide ratio of 1/10, whereby a tinting shade coating composition was prepared. The tinting shade coating composition was viscosity-adjusted with xylene to show 20 seconds (25° C.) with a ford cup, and the adjusted coating composition was placed in a test tube. When the glass wall of the test tube was observed for a change, the coating compositions containing the pigment dispersing agents of the present invention showed a small color separation with the passage of time as compared with the coating compositions in Comparative Examples.

TABLE 2

| Ex. CEx. | Pigment | Pigment dispersing agent | Amount ratio of pigment/pigment dispersing agent | Fluidity (cps) 6 rpm | Fluidity (cps) 60 rpm | TI value | Gloss % 20°G | Color difference ΔE |
|---|---|---|---|---|---|---|---|---|
| CEx.1 | C.I. Pigment | — | 100/0 | 7,880 | 2,160 | 3.65 | 65.5 | STD |
| CEx.2 | Blue 15:1 | m | 95/5 | 580 | 530 | 1.09 | 82.0 | 0.87 |
| Ex.1 | (Phthalo- | a | 95/5 | 550 | 500 | 1.10 | 82.5 | 0.23 |
| Ex.2 | cyanine pigment) | b | 95/5 | 530 | 480 | 1.10 | 84.0 | 0.19 |
| CEx.3 | C.I. Pigment | — | 100/0 | 3,500 | 1,020 | 3.43 | 69.8 | STD |
| CEx.4 | Green 36 | m | 95/5 | 400 | 355 | 1.13 | 80.1 | 1.65 |
| Ex.3 | (Phthalo- | e | 95/5 | 300 | 280 | 1.07 | 84.3 | 0.20 |
| Ex.4 | cyanine pigment) | f | 95/5 | 380 | 365 | 1.04 | 83.0 | 0.25 |
| CEx.5 | C.I. Pigment | — | 100/0 | 5,680 | 1,150 | 4.94 | 65.0 | STD |
| CEx.6 | Red 122 | n | 95/5 | 400 | 380 | 1.05 | 84.0 | 0.58 |
| Ex.5 | (Quina- | c | 95/5 | 310 | 310 | 1.00 | 84.3 | 0.12 |
| Ex.6 | cridone pigment) | l | 90/10 | 540 | 520 | 1.04 | 83.7 | 0.18 |
| CEx.7 | C.I. Pigment | — | 100/0 | 2,920 | 1,190 | 2.45 | 66.2 | STD |
| CEx.8 | Red 254 | n | 95/5 | 540 | 500 | 1.40 | 81.3 | 1.43 |
| Ex.7 | (Diketo- | h | 95/5 | 440 | 420 | 1.05 | 83.1 | 0.28 |
| Ex.8 | pyrropyrrol pigment) | k | 90/10 | 410 | 410 | 1.00 | 84.0 | 0.24 |
| CEx.9 | C.I. Pigment | — | 100/0 | 3,350 | 1,590 | 2.11 | 64.2 | STD |
| CEx.10 | Red 177 | n | 95/5 | 400 | 380 | 1.05 | 83.2 | 1.18 |
| Ex.9 | (Anthra- | g | 95/5 | 300 | 300 | 1.00 | 86.0 | 0.25 |
| Ex.10 | quinone pigment) | j | 90/10 | 330 | 330 | 1.00 | 84.8 | 0.30 |
| CEx.11 | C.I. Pigment | — | 100/0 | 8,950 | 1,890 | 4.73 | 69.2 | STD |
| Ex.11 | Red 178 | a | 95/5 | 400 | 400 | 1.00 | 84.0 | 0.18 |
| Ex.12 | (Perylene | d | 90/10 | 640 | 600 | 1.07 | 81.5 | 0.24 |
| Ex.13 | pigment) | i | 95/5 | 440 | 440 | 1.00 | 82.2 | 0.22 |
| CEx.12 | C.I. Pigment | — | 100/0 | 3,520 | 1,350 | 2.61 | 68.2 | STD |
| Ex.14 | Violet 23 | f | 90/10 | 610 | 580 | 1.05 | 82.0 | 0.10 |
| Ex.15 | (Dioxadine pigment) | h | 90/10 | 550 | 550 | 1.00 | 83.5 | 0.15 |
| CEx.13 | C.I. Pigment | — | 100/0 | 2,920 | 1,020 | 2.86 | 70.2 | STD |
| Ex.16 | Yellow 154 | a | 90/10 | 420 | 400 | 1.05 | 84.0 | 0.27 |
| Ex.17 | (Benzimid- azolone pigment) | i | 90/10 | 400 | 400 | 1.00 | 84.2 | 0.31 |
| CEx.14 | C.I. Pigment | — | 100/0 | 11,400 | 4,200 | 2.71 | 65.2 | STD |
| Ex.18 | Yellow 14 | a | 90/10 | 3,420 | 1,840 | 1.86 | 81.0 | 0.21 |
| Ex.19 | (Disazo pigment) | e | 90/10 | 3,840 | 2,060 | 1.86 | 80.2 | 0.25 |
| CEx.15 | C.I. Pigment | — | 100/0 | 9,580 | 3,430 | 2.79 | 61.8 | STD |

TABLE 2-continued

| Ex. CEx. | Pigment | Pigment dispersing agent | Amount ratio of pigment/ pigment dispersing agent | Fluidity (cps) 6 rpm | 60 rpm | TI value | Gloss % 20°G | Color difference ΔE |
|---|---|---|---|---|---|---|---|---|
| Ex.20 | Black 7 | e | 95/5 | 720 | 650 | 1.11 | 83.0 | 0.08 |
| Ex.21 | (Carbon pigment) | j | 95/5 | 800 | 750 | 1.07 | 81.2 | 0.11 |

Ex. = Example, CEx. = Comparative Example
Fluidity: Measured with Brookfield viscometer at 20° C. TI value = Viscosity at 6 rpm/ viscosity at 60 rpm
Color difference: Difference from product of a pigment alone (ΔE value)

The pigment compositions containing the above pigment dispersing agents (a) to (l) caused no aggregation when used in nitrocellulose lacquer acrylic resin coating compositions and gravure inks, and they thus showed excellent fluidity.

As explained above, when the pigment dispersing agent of the present invention, not only the pigment composition is excellent in freedom of aggregation, non-crystallizability and fluidity, but also an ink and a coating composition excellent in gloss and hue can be obtained.

What is claimed is:

1. A pigment composition containing at least one pigment selected from the group consisting of a phthalocyanine pigment, a quinacridone pigment, an isoindolinone pigment, a perylene-perinone pigment, a dioxadine pigment, a diketopyrrolopyrrole pigment, an anthraquinone pigment, a benzoimidazolone pigment, an azo pigment and an inorganic pigment and a pigment dispersing agent of the formula

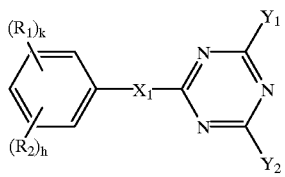

(1)

wherein $X_1$ is $-NR_3$ or $-O-$, $R_1$ is an amino group, $R_2$ is a halogen atom, an amino group, a nitro group, a hydroxyl group, an alkoxy group, a carboxyl group, a sulfonic acid group, a substituted or non-substituted alkyl group, a substituted or non-substituted alkenyl group, $R_3$ is a hydrogen atom, a substituted or non-substituted alkyl group or, a substituted or non-substituted alkenyl group, $Y_1$ is a group of the formulae (2) to (5), $Y_2$ is a hydroxyl group, an alkoxy group, $Y_1$ or a group of the formula (6), k is an integer of 1 to 3 and h is an integer of 0 to 2 formula (2):

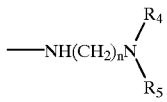

(2)

wherein each of $R_4$ and $R_5$ is independently substituted or non-substituted alkyl group or a substituted or non-substituted alkenyl group or together they represent a five or six-membered ring which may contain a nitrogen atom, an oxygen atom or a sulfur atom, and n is an integer of 1 to 6, formula (3):

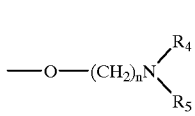

(3)

wherein $R_4$ and $R_5$ are as defined in the formula (2), formula (4):

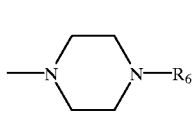

(4)

wherein $R_6$ is substituted or non-substituted alkyl group or a substituted or non-substituted alkenyl group, formula (5):
—NH(CH$_2$)$_p$

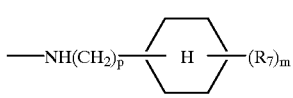

(5)

wherein $R_7$ represents a group of the formula (4) or a group of the formula (7), p is an integer of 0 to 6 and m is an integer of 1 or 2, formula (6):

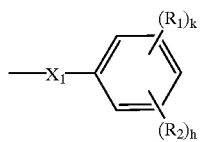
(6)

wherein $X_1$, $R_1$, $R_2$, k and h are as defined in the formula (1), formula (7):

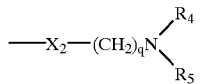
(7)

wherein $X_2$ is a direct bond, —NH— or —O—, q is an integer of 0 to 6 and $R_4$ and $R_5$ are as defined in the formula (2) and wherein the amount of the pigment dispersing agent of formula (1) per 100 parts by weight of the pigment is 0.1 to 30 parts by weight.

2. The pigment composition of claim 1, wherein $Y_1$ is the group of the formula (2).

3. The pigment composition of claim 1, wherein $Y_1$ is the group of the formula (2) and each of $R_4$ and $R_5$ is an alkyl group having 1 to 6 carbon atoms.

4. The pigment composition of claim 1, wherein $X_1$ is —NH, $Y_1$ is the group of the formula (2) and each of $R_4$ and $R_5$ is an alkyl group having 1 to 6 carbon atoms.

* * * * *